US009867676B2

(12) United States Patent
Ertugrul et al.

(10) Patent No.: US 9,867,676 B2
(45) Date of Patent: Jan. 16, 2018

(54) DENTAL PREPARATION INSTRUMENT WITH A PNEUMATIC TURBINE

(71) Applicant: Sirona Dental Systems GmbH, Bensheim (DE)

(72) Inventors: Metin Ertugrul, Rodermark (DE); Siegfried Goisser, Einhausen (DE)

(73) Assignee: DENTSPLY SIRONA INC., York, PA (US)

( * ) Notice: Subject to any disclaimer, the term of this patent is extended or adjusted under 35 U.S.C. 154(b) by 0 days.

(21) Appl. No.: 14/767,198

(22) PCT Filed: Nov. 2, 2014

(86) PCT No.: PCT/EP2014/052586
§ 371 (c)(1),
(2) Date: Aug. 11, 2015

(87) PCT Pub. No.: WO2014/122316
PCT Pub. Date: Aug. 14, 2014

(65) Prior Publication Data
US 2016/0000521 A1    Jan. 7, 2016

(30) Foreign Application Priority Data
Feb. 11, 2013   (DE) .................. 10 2013 202 174

(51) Int. Cl.
*A61C 1/05*    (2006.01)
*A61C 1/18*    (2006.01)

(52) U.S. Cl.
CPC .............. *A61C 1/052* (2013.01); *A61C 1/057* (2013.01); *A61C 1/186* (2013.01)

(58) Field of Classification Search
CPC .. A61C 1/02; A61C 1/05; A61C 1/052; A61C 1/057; A61C 1/186; A61C 1/181; F04D 5/00; F04D 17/06; F04D 29/42
(Continued)

(56) References Cited

U.S. PATENT DOCUMENTS 2,817,296 A * 12/1957 Fabig .................. F04D 5/00
                                                415/56.1
3,733,143 A *  5/1973 Theis, Jr. ............ F01D 15/065
                                                415/123
(Continued)

FOREIGN PATENT DOCUMENTS

CH    689 796 A5    11/1999
DE    43 20 532 C1   9/1994
(Continued)

OTHER PUBLICATIONS

International Preliminary Report on Patentability dated Aug. 11, 2015, in International Application No. PCT/EP2014/052586.
(Continued)

*Primary Examiner* — Nicholas Lucchesi
*Assistant Examiner* — Shannel Wright
(74) *Attorney, Agent, or Firm* — Douglas J. Hura; Leana Levin; David A. Zdurne

(57) ABSTRACT

A dental preparation instrument having a pneumatic turbine (1) with a rotor (5) for driving a tool (1.1), wherein the rotor (5), which is mounted in a turbine chamber (18) for rotation about an axis of rotation (4), is impinged by compressed air from a compressed-air nozzle (22). A first radial partition (23) has an opening (17) via which an annular space (8) is in flow connection with an outlet duct (19).

4 Claims, 2 Drawing Sheets

(58) Field of Classification Search
USPC .......................................................... 415/904
See application file for complete search history.

(56) References Cited

U.S. PATENT DOCUMENTS

| | | | | |
|---|---|---|---|---|
| 4,336,002 | A * | 6/1982 | Rose | .................. F04D 5/00 |
| | | | | 417/203 |
| 5,334,013 | A * | 8/1994 | Meller | .................. A61C 1/05 |
| | | | | 415/904 |
| 5,486,092 | A * | 1/1996 | Borg | .................. F04D 5/00 |
| | | | | 415/182.1 |
| 5,496,173 | A | 3/1996 | Wohlgemuth | |
| 5,567,154 | A * | 10/1996 | Wohlgemuth | .......... A61C 1/05 |
| | | | | 415/904 |
| 5,807,108 | A * | 9/1998 | Schwenoha | ............ A61C 1/05 |
| | | | | 415/904 |
| 6,120,291 | A | 9/2000 | Bareth et al. | |
| 7,329,123 | B2 | 2/2008 | Tanaka et al. | |
| 7,927,101 | B2 | 4/2011 | Takashi et al. | |
| 8,721,333 | B2 | 5/2014 | Takashi et al. | |
| 2004/0005528 | A1 * | 1/2004 | Jikuhara | .................. A61C 1/05 |
| | | | | 433/132 |
| 2006/0121413 | A1 * | 6/2006 | Turner | .................. A61C 1/05 |
| | | | | 433/114 |
| 2007/0065774 | A1 * | 3/2007 | Pernot | .................. A61C 1/08 |
| | | | | 433/126 |
| 2009/0029312 | A1 * | 1/2009 | Takashi | .................. A61C 1/05 |
| | | | | 433/132 |
| 2010/0055642 | A1 * | 3/2010 | Rothenwaender | ....... A61C 1/05 |
| | | | | 433/99 |
| 2013/0266430 | A1 * | 10/2013 | Hasegawa | ............. A61C 1/057 |
| | | | | 415/182.1 |

FOREIGN PATENT DOCUMENTS

| | | |
|---|---|---|
| DE | 692 01 133 T2 | 8/1995 |
| DE | 44 28 039 C1 | 11/1995 |
| DE | 195 18 703 A1 | 2/1996 |
| DE | 103 20 903 A1 | 11/2003 |
| DE | 11 2006 000 658 T5 | 2/2008 |
| DE | 10 2010 049 522 A1 | 6/2011 |
| EP | 0 629 383 B1 | 12/1994 |
| EP | 0 830 848 A1 | 3/1998 |
| EP | 0 974 308 A1 | 1/2000 |
| EP | 0997110 A2 * | 5/2000 ................ A61C 1/05 |

OTHER PUBLICATIONS

International Search Report dated Jul. 7, 2014, in International Application No. PCT/EP2014/052586.

Office Action dated Aug. 1, 2013, in German Patent Application No. 10 2013 202 174.7.

* cited by examiner

DENTAL PREPARATION INSTRUMENT WITH A PNEUMATIC TURBINE

TECHNICAL FIELD

The invention relates to a dental preparation instrument having a pneumatic turbine with a rotor for driving a tool, wherein the rotor, which is mounted in a turbine chamber for rotation about an axis of rotation, is impinged by compressed air from a compressed-air nozzle and has adjusting means for regulating speed, wherein an annular duct that is flow-connected to the turbine chamber is arranged on the side of the turbine chamber facing the tool, the annular duct extending over an angular range of the perimeter of the turbine chamber and having a first radial partition facing the outlet duct in the region of the compressed air nozzle, and having a second radial partition at the end of the angular range at a distance from the outlet duct as well as an annular partition which is interrupted in the region of the outlet duct, and an additional annular duct exists radially to the inside of the first annular duct which is open to the outlet duct in the region of the interrupted partition, wherein a disk-shaped partition exists between the two radial partitions and extends in the peripheral direction over the remaining angular range, and the disk-shaped partition seals off the turbine chamber from the outlet duct.

PRIOR ART

DE 195 18 703 A1 describes a dental drive unit having a shaft which can be made to rotate, wherein supplied compressed air, after performing work on the rotor, passes from the rotor chamber into an annular space, and from there into a first chamber. To pass from the annular space into the first chamber, the exhaust air must flow through a passage which is bordered by the rotor and a partition which is cylindrical in sections. To limit the idle speed, a variably-shaped, elastic adjusting means is integrated in the rotor, wherein this adjusting means reduces and possibly entirely closes the cross-sectional area of the passage in idle mode at the maximum speeds as a result of centrifugal forces. Because the region of the rotor having the greatest diameter is closed to the outlet opening and the return air duct in idle mode and only opens again as a result of decreasing rotational speed, a pressure gradient after closing arises in idle mode between the outer edge of the rotor and the regions of the rotor near the axis up to the return air duct, which can intensify an undesirable suction effect by the dental turbines in the deceleration phase.

A turbine handpiece is known from EP 0 974 308 A1 having a flow web that, in cooperation with the flow of pressurizing medium also rotating within the turbine chamber, forms a curtain in front of the outlet opening in the turbine chamber. The flow is deflected enough by the flow web radially to the inside of the turbine chamber opposite the outlet direction that it is prevented from exiting the outlet opening and consequently remains in the turbine chamber. This makes it difficult for a flow favorable to suction to form while slowing down. A disadvantage is that the flow web extends over the entire outlet opening, and a loss of output and restriction of the configuration of the outlet opening and especially the outlet cross-section can be expected.

A chamber is known from DE 103 20 903 A1 which borders a turbine chamber. The air is pressed into this chamber by centrifugal force, which thereby generates a locally limited overpressure curve. From this chamber, an ancillary flow runs past the bottom side and top side of the rotor to the openings in the bearing. The pressure cushion generated in this chamber is dependent on the rotational speed and exists both during operation and slowdown, during which, however, it decreases along with the speed. The suction effect is to be counteracted thereby during slowdown as well.

Braking means are known from DE 692 01 133 T2 for braking or stopping the rotor. The braking means are actuated by a control flow of a fluid and comprise an elastically deformable organ having application means and counter-application means which brake the rotation of the rotor by means of friction. Due to the high speeds, the friction contact generates a great deal of heat, and abrasion occurs so that, over time, the effect of the brake is reduced by wear phenomena. In addition, the interior of the rotor becomes contaminated by the abraded material. These particles can also enter the patient's mouth, which is also undesirable.

An outflow chamber is known from EP 0 629 383 B1 which is positioned on the side of the rotor facing the tool. An outflow duct borders this tool-side outflow chamber which is arranged near the axis of the tool-side rotor shaft and runs towards the tool-side rotor bearing and has an opening to the returning air duct. With this arrangement of the outflow chamber, outflow duct and return air outlet, the region of the rotor having the largest diameter is separate from the return air outlet. The air centrifuged radially outward by the rotor during slowdown cannot flow out. In the region of the return air outlet, there are no notable differences in the diameter, which proves to be extremely effective in regard to reducing the suction effect. A significant disadvantage of this invention is the necessarily unfavorable design of the return air guideway because all of the exhaust air must flow through the outflow chambers to reach the return air duct. On the one hand, this greatly reduces the minimum cross-section through which the exhaust air must flow and produces a back-up in the rotor chamber. On the other hand, the exhaust air must flow radially out of the rotor chamber having the largest diameter in opposition to centrifugal force toward the outflow duct which is positioned near the axis and has a small diameter. This is associated with disadvantageous losses in output.

The object of the invention is to reduce the suction of the rotor during slowdown, i.e., without being driven.

DISCLOSURE OF THE INVENTION

According to the invention, this object is achieved with the features of claim 1 in that the first radial partition has an opening by means of which the annular space is flow-connected to the outlet duct.

The opening in the partition of the first annular space prevents suction during slowdown and offers a very easily producible and hence economical solution without parts subject to wear and without significant sacrifices in output at the rated rotational speed. During slowdown, a guided flow from the second annular duct into the first annular duct is used to block flow to thereby prevent suction through the bearing during slowdown.

Advantageously, an adjusting means which is deformable depending on the speed can be provided that deforms at a high rotational speed under the effect of centrifugal force, wherein the adjusting means is arranged in a seat area in the rotor, and wherein the seat area is covered by a control ring while forming a gap, wherein the control ring has at least one passage to the second annular duct, and wherein an additional gap exists between the control ring and the axial partition.

By dividing the flow, it is possible to provide strong output in preparation mode when the gaps are open, and to limit the rotational speed during idle mode by partially or completely closing the gap between the rotor and the control ring. Rather, the gap between the control ring and axial partition ensures a minimal flow cross-section which still definitely exists even when the adjusting means is deformed.

The control function of the idling rotational speed via the adjusting means and via the control ring is fully independent of the opening in the partition of the first annular gap and is not impaired by it; furthermore, it is expressly noted that the control function can also be used in a preparation instrument which is designed without this opening in the first partition.

Advantageously, the adjusting means can be deformable such that it closes the gap between the control ring and the rotor by elastic deformation at a high rotational speed, preferably starting at a speed of 250,000 rpm, and under a load status with a lower rotational speed, preferably less than a rotational speed of 200,000 rpm, the gap between the control ring and rotor is free from being restricted in flow by the adjusting means.

In these regions, a sufficient supply of output is possible while simultaneously avoiding bearing stress from excessive rotational speeds.

Advantageously, the opening in the partition can take up at least 20% of the cross-section of the annular duct, and preferably more than 60% of the cross-section.

This can reduce suction during slowdown and nevertheless minimize sacrifices in output at the nominal rotational speed. It has been demonstrated that even completely opening the annular duct by opening 100% of the partition yields satisfactory results in practice.

BRIEF DESCRIPTION OF THE DRAWINGS

The device according to the invention will be explained with reference to the drawings. In the drawings.

EMBODIMENT OF THE INVENTION

Figure 1:
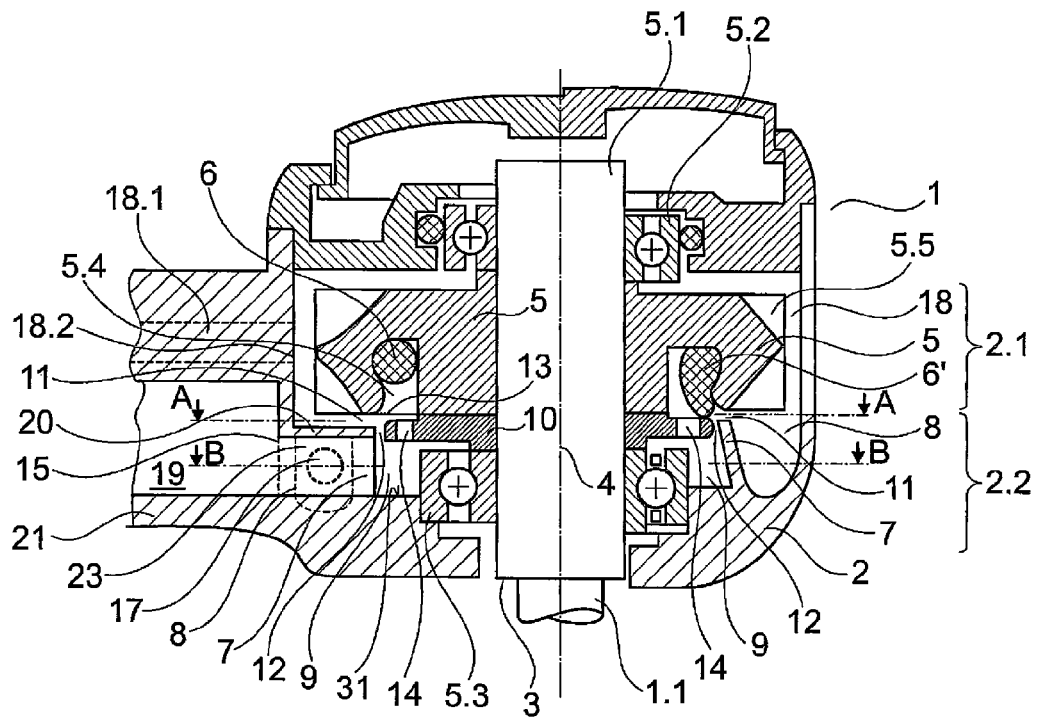
FIG. 1 shows a longitudinal section of a dental preparation instrument having a pneumatic turbine divided into a right side and a left side.

FIG. 1 shows a dental preparation instrument having a pneumatic turbine 1, for driving a tool 1.1, that has a rotor 3, which is mounted in a head housing 2, and a rotor 5 that is rotatable about a rotational axis 4, as well as a shaft 5.1 bearing the rotor 5, and bearings 5.2, 5.3 arranged on both sides of the rotor 5 to bear the shaft 5.1 in the head housing 2.

On one of its two front faces, the rotor 5 has an annular peripheral seat area 5.4 for an adjusting means 6—in this case on the bottom side facing the tool (not shown)—which in the portrayed embodiment is designed as an O-ring that is elastically deformable under the effect of rotational speed.

The compressed air used to drive the rotor is diverted by blades 5.5 on the rotor and flows off of them.

The adjusting means 6 is shown undeformed on the left side of FIG. 1 divided along the rotational axis 4; on the right side of FIG. 1, the adjusting means 6' is elastically deformed under the influence of the rotational speed.

The rotor 5 is arranged in a turbine chamber 18 in the head housing 2 in which a compressed air duct 18.1 terminates that is guided through the head housing 2 along with a return air duct 19 that is also guided through the head housing 2, but which is also at an axial distance from the compressed air duct 18.1 with respect to the rotational axis 4, wherein the outlet opening 15 of the return air duct 19 lies below the compressed air opening 18.2 of the compressed air duct 18.1, i.e., facing the tool (not shown). The compressed air duct 18.1 and the return air duct 19 are in a handle 21 of the head part 2 which transitions into the head part 2.

In a bottom region which faces the tool 1.1, the turbine chamber 18 has a first annular partition 7, which is only interrupted in a region corresponding to the outlet opening 15, and which has a lateral surface coaxial to the rotational axis 4 to delimit a first exterior annular duct 8 and a disk-shaped partition 20 that transition into each other and extend over part of the perimeter. The partition 20 is arranged in the region of the outlet opening 15 and the compressed air opening 18.2, and the annular duct 8 extends from the compressed air opening 18.2, along an angular range to at least an angle of 90°, preferably by an angle of up to 320° (see FIGS. 2 and 3 below).

Radially to the inside toward the partition 7 arranged in the bottom region of the turbine chamber 18, there is a second annular duct 9, which is bordered by the bearing 5.3 in a radial direction that is supported in the head housing 2. As shown on the left side in FIG. 1, this annular duct 9 is axially delimited by the disk-shaped partition 20 and is flow-connected to the outlet duct 19 by the cutout in the partition 7 and by the outlet opening 15.

The bottom region 2.2 of the turbine chamber 18 arranged in the head housing 2 has a height which is 20% to 75% of the overall height of the region 2.1 taken up by the rotor 5. Between the rotor 5 and annular partition 7, a gap 11 is formed which is designated as the main cross-sectional area $A_0$ for the outflow of compressed air supplied to the turbine chamber 18 away from the rotor 5 and toward the outlet opening 15 that limits the maximum possible airflow of the turbine because all of the air used for driving the rotor 5 must first pass through this gap 11.

Arranged between the bottom bearing 5.3 and rotor 5 is a control ring 10, which, like the bearing 5.3 and rotor 5, is also supported on the shaft 5.1. This control ring 10 is arranged in the turbine chamber 18 at the transition of the region 2.2 holding the rotor 5 to the region 2.1 in which the annular ducts 8, 9 are arranged. The radial extension of the control ring 10 proceeds up to the radial partition 7, wherein a gap exists, having a cross-sectional area which is designated as the control cross-sectional area $A_1$ and which is less than the main cross-sectional area $A_0$.

The compressed air flowing from the rotor 5, also termed the return air, passes through the axial gap 11 between the rotor 5 and annular partition 7 to the radial gap 12 between the partition 7 and control ring 10, and passes entirely into the annular gap 9 leading to the outlet opening depending on the operating state as shown in the right half of FIG. 1 at a high speed. Opposite the main cross-sectional area, there is a reduction of the cross-section, and the theoretically possible high rotational speeds across the main cross-sectional area are limited by the control cross-sectional area of the gap 12.

In the operating state at a low speed as shown in the left half of FIG. 1, the return air flows through the gap 12 between the annular partition 7 in the control ring 10 as well as through a gap 13 between the control ring 10 and the seat area 5.4 arranged in the rotor 5 for the rotational-speed-dependent adjusting means 6. This gap 13 can have a large-size cross-sectional area, which can even be larger than the main cross-sectional area because the return air flowing into the seat area 5.4 can exit into the second annular space 9 via a passage 14 arranged in the control ring 10 or through a plurality of passages arranged and distributed over the perimeter. The gap 13 thereby provides a regulating cross-sectional area $A_2$ because the cross-sectional area of the passage or passages 14 is larger in size.

While idling, i.e., without a load and at high rotational speeds, the actual effective cross-sectional area $A_{eff}$ corresponds to the control cross-sectional area $A_1$ because the gap 13 is closed by the deforming adjusting means. While operating under a load, i.e., when gripping a tool for shaping a tooth, the rotational speed first decreases, and the gap 13 is opened depending on the rotational speed. The regulating cross-sectional area is dimensioned such that, when completely open together with the control cross-sectional area, at least the main cross-sectional area is provided. The effective cross-sectional area consists of both the control cross-sectional area as well as the rotational-speed-dependent regulating cross-sectional area.

From the second annual duct 9, the return air flows under the disk-shaped partition 20 in the radial direction past the annular duct 8, wherein in a radial partition 23 for separating the annular duct 8 in the region of the outlet opening 15, a passage 17 is provided through which the return air can flow back into the first annular duct 8, for example, during slowdown.

Figure 2:
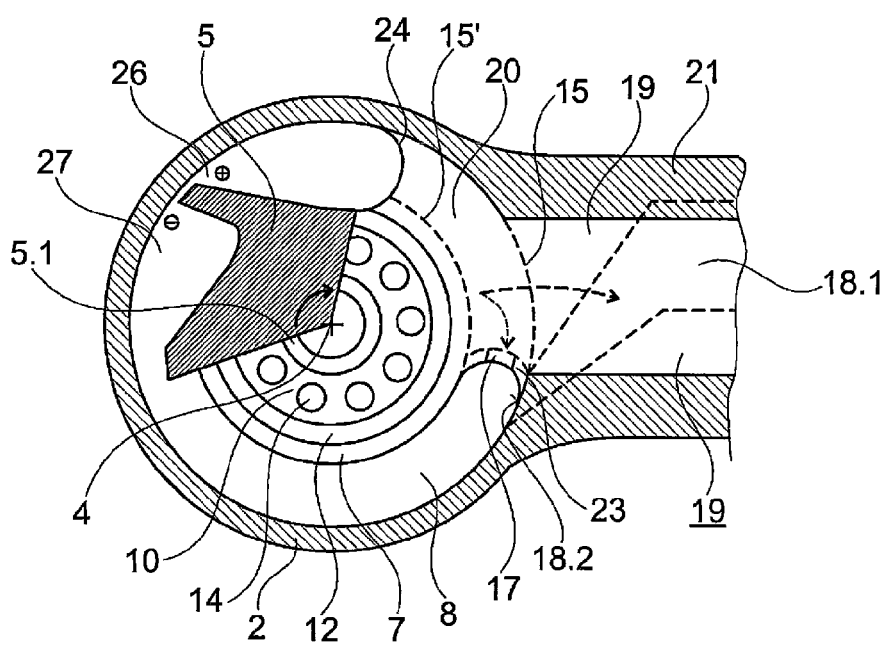
FIG. 2 shows a section along line AA from FIG. 1.

FIG. 2 shows a section running transversally through the head housing 2 at the height of the gap 11, i.e., between the rotor 5 shown cutaway which lies above the sectional plane and the control ring 10 lying below the sectional plane. In the control ring 10, the passages 14 are visible which are arranged and distributed over the perimeter. The control ring 10 is attached to the shaft 5.1 and rotates with it about the rotational axis 4. Located in the outer perimeter of the control ring 10 is the gap 12 to the annular partition 7, which delimits the annular duct 8 radially to the inside. The radially outer limit of the annular duct 8 is formed by the head housing 2. The annular duct 8 has a radial partition 23 lying to the front in the direction of flow of the compressed air, and it separates the annular duct 8 from the outlet opening 15. However, a passage 17 is arranged in the partition 23, through which return air can flow into the annular duct 8, as indicated by an arrow pointing toward the flow opening 17. Viewed downward in the direction of flow, the annular duct is delimited by a second radial partition wall 24.

It should be noted that in the region of the outlet opening 15, the annular duct 8 is interrupted by the radial partitions 23, 24 and by the disk-shaped partition 20 so that no air can pass from the annular space 8 itself into the return air duct 19; rather, the return air flows through the gap 12 and possibly through the passages 14 in the control ring 10 into the region below the disk-shaped partition 20 and between the radial partitions 23, 24, and from there through the outlet opening 15 into the return air duct 19 indicated by the long dashed arrow.

Above the plane of the drawing and hence above the sectional plane, the drive air duct 18.1 routed through the handle 21 to the head housing 2 is indicated by a dashed line as is the position of the compressed air opening 18.2, which can also be termed the compressed air nozzle. The compressed air flows through the compressed air opening 18.2 into the turbine chamber and drives the rotor.

The suction side 26 and pressure side 27 of the rotor 5 are provided with corresponding pressure signs during slowdown as described. During operation when the compressed air pressure is turned on, the signs are reversed.

Figure 3:
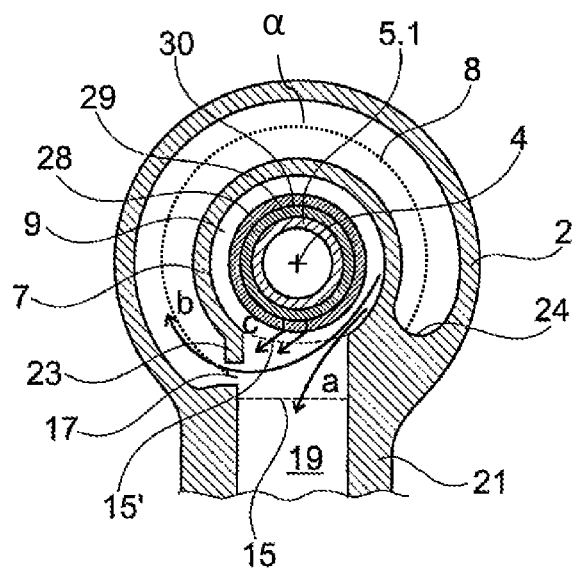
FIG. 3 shows a section along line BB from FIG. 1.

FIG. 3 shows a section of the head housing 2 below the disk-shaped partition 20 from FIGS. 1 and 2 which is therefore not shown. Proceeding from the head housing 2, which transitions into the handle 21, the annular space 8 is shown with the radial partitions 23, 24, which are delimited toward the axis 4 by the partition 7. The partition 7 delimits the annular space 9 extending further to the inside and, toward the return air duct 19, is interrupted by the outlet opening 15'. The outlet opening 15 is arranged at the transition from the head housing 2 to the handle 21 for the return air duct 19, as already shown in FIG. 1.

In the radial direction, the annular space 9 is delimited by the bearing 5.3 with the bearing outer ring 28 arranged on the shaft 5.1, and the radial partition 7 and outlet opening 15', wherein the bearing 5.3 also has a bearing gap 30 and a bearing inner ring 29. In the axial direction, the annular space 9 is delimited at the top by the control ring 10 with the passages 14 and the gap 12, and at the bottom to the tool side by the bearing 5.3 and an annular duct floor 31 (FIG. 1).

Arrows a, b and c indicate flow paths for the airflow during slowdown, which will be explained further. The arrow "a" designates the return air which flows from the annular space 9 through the outlet opening 15'. The arrow "b" designates the return air which flows from the annular space 9 through the passage 17 in the partition 23 into the annular space 8. The arrow "c" designates the air that, where applicable, can be drawn through the bearing gap 30 into the return air duct 19 and is retarded, or whose generation is even suppressed.

At the suction side of the blades when passing by the blades of the rotor 5, the passage 17 in the radial partition of the annular duct 8 continuously generates suction from the region of the return air duct 19 or the outlet opening 15 in the first annular duct 8. The passage 17 accordingly connects the flow of the first annular duct 8 to the return air duct 19 with the outlet openings 15, 15'.

On the suction side of the blades of the rotor 5, air particles are entrained below the control disk 10 in FIG. 2 in the region of the outlet duct 19. This gives rise to a flow according to arrow "b" from the second annular space 9 to the first annular space 8 transverse to the return air duct 19 in the direction of rotation of the rotor 5. This forced flow according to arrow "b" extends across the outlet opening 15' and functions to a certain extent like a barrier between the return air chamber 19 and the annular space 9 in which the rotating components are located.

Due to this forced flow, the return air duct 19 is closed to flow in the region of the outlet opening 15, and an acceleration of the air which could be sucked through the bearing gap 30 during slowdown is prevented.

Figure 4:
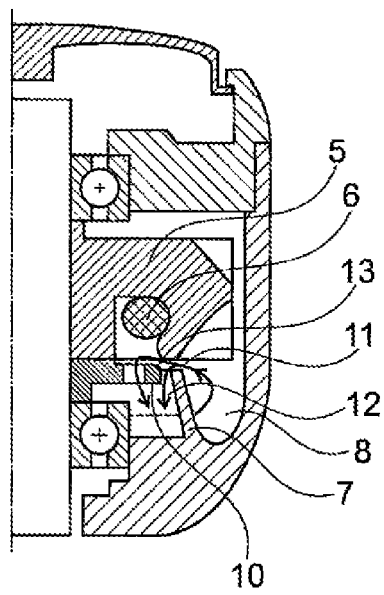
FIG. 4 shows the guided flow in load mode at the nominal speed in detail.
Figure 5:
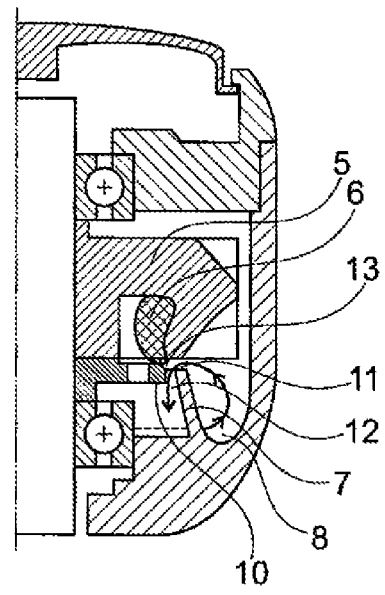
FIG. 5 shows the guided flow in idle mode in detail.
Figure 6:
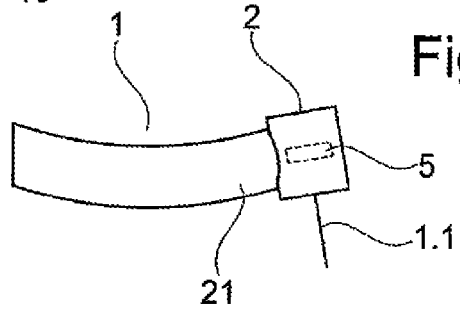
FIG. 6 shows a schematic drawing of the preparation instrument as an overall depiction.

FIGS. 4 and 5 show two different flow states, i.e., at a low rotational speed and at a high rotational speed of the rotor 5. Fundamental to the difference in the flow state is the rotational-speed-dependent deformation of the adjusting means 6 as already explained with reference to FIG. 1. At high rotational speeds, the gap 13 between the control ring 10 and rotor 5 is closed by deformation of the adjusting means 6, as depicted in FIG. 5, whereas the gap 13 is open at low speeds as depicted in FIG. 4. When the gap 13 is opened, as shown in FIG. 4, the flow of return air originating from the annular gap 8 and flowing through the gap 11 formed as the main cross-sectional surface between the rotor 5 and the annular partition 7 divides and flows through the gap 13 as well as the gap 12 between the control ring 10 and partition 7.

When the gap 13 is closed as shown in FIG. 5, only the gap 12, which has a cross-sectional area that is smaller than the gap 11, is available as a flow path following gap 11. This ensures that the entire amount of air required to apply torque at a low rotational speed under a load cannot flow through; instead only a part of this amount of air can flow through, which causes a limitation in the rotational speed of the rotor during idle mode.

The separation of the exhaust air into two components, on the one hand through an unchanging first cross-section at the gap 12 and on the other hand through a second cross-section at the gap 13, which is regulated depending on the rotational speed, enables a highly efficient limitation of the idle rotational speed with only a minimum loss of output.

Even though the adjusting means 6 together with the partition 7 and 20 partially close off the turbine chamber 18 from the region of the rotor 5 near the axis over the gap 13 in idle mode, this gap 13 is completely open during slowdown as the rotational speed falls. An unrestricted air path exists between the region of the rotor 5 with the greatest diameter, i.e., at the outer edge of the rotor and the outlet opening 15 of the return air duct 19. Without the passage 17 according to the invention, there exists an elevated danger of suction through the bottom bearing during slowdown.

The invention claimed is:

1. A dental preparation instrument, comprising
   a pneumatic turbine that includes a rotor configured to rotate about a longitudinal axis;
   a turbine chamber that includes a compressed air duct opening and an outlet air duct opening, wherein the rotor is mounted in the turbine chamber such that compressed air from the compressed air duct opening impinges on at least a part of the rotor;
   a first annular duct that is flow-connected to the turbine chamber and is arranged on a side of the turbine chamber,
   wherein the first annular duct extends over an angular range of a perimeter of the turbine chamber, from a first end to a second end,
   wherein the first annular duct includes:
      (i) a first radial partition facing the outlet duct opening in a region of the compressed air duct opening, and provided at the first end of the first annular duct,
      (ii) a second radial partition distanced from the outlet air duct opening, and provided at the second end of the first annular duct, and
      (iii) an annular partition which is interrupted in a region of the outlet air duct opening, and
   wherein the first radial partition has a passage which connects an annular space inside the first annular duct to the outlet air duct opening;
   a second annular duct arranged to an inside, in a radial direction, of the first annular duct, wherein the second annular duct is open to the outlet air duct opening in a region of the outlet air duct opening; and
   a disk-shaped partition arranged between the first radial partition and the second radial partition,
   wherein the disk-shaped partition extends in a peripheral direction over a second angular range that is equal to 360° less the angular range over which the first annular duct extends, and
   wherein the disk-shaped partition seals the turbine chamber from the outlet air duct opening; and
   wherein a deformable adjusting element is arranged in a seat area in the rotor,
   wherein the deformable adjusting element is covered by a control ring while forming a gap between the control ring and the rotor,
   wherein the control ring has at least one passage to the second annular duct, and wherein an additional gap exists between the control ring and the annular partition; and
   wherein the deformable adjusting element is deformed when a rotational speed of the rotor is equal to or greater than 250,000 rpm such that it closes the gap between the control ring and the rotor, and
   wherein the deformable adjusting element is not deformed when a rotational speed of the rotor is less than 200,000 rpm and a flow of air in the gap between the control ring and rotor is not restricted.

2. The dental preparation instruments according to claim 1, wherein the passage in the first radial partition is at least 20% of a cross-section of the first annular duct.

3. The dental preparation instrument according to claim 1, further comprising:
   a tool configured to receive a rotational force from the rotor,
      wherein the side of the turbine chamber, on which the annular duct is arranged, faces the tool.

4. The dental preparation instrument according to claim 1, wherein the passage in the first radial partition is at least 60% of a cross-section of the first annular duct.

* * * * *